(12) United States Patent
Evans et al.

(10) Patent No.: US 6,472,548 B2
(45) Date of Patent: Oct. 29, 2002

(54) PROCESS FOR PREPARING A COMPLEX OF A LIGAND, METAL AND BASE

(75) Inventors: Clare Evans, Moreton Wirral (GB); Peter Michael Radley, Chester (GB); Sarah E. Worsley, Chester (GB)

(73) Assignee: Associated Octel Company Limited, Manchester (GB)

( * ) Notice: Subject to any disclaimer, the term of this patent is extended or adjusted under 35 U.S.C. 154(b) by 0 days.

(21) Appl. No.: 09/850,663

(22) Filed: May 7, 2001

(65) Prior Publication Data

US 2002/0032343 A1 Mar. 14, 2002

Related U.S. Application Data

(60) Provisional application No. 60/204,074, filed on May 12, 2000.

(51) Int. Cl.$^7$ ................................................ C07F 15/02
(52) U.S. Cl. ...................................................... 556/148
(58) Field of Search ......................................... 556/148

(56) References Cited

U.S. PATENT DOCUMENTS 5,679,817 A * 10/1997 Sakai et al.
5,717,123 A    2/1998 St. George et al.

FOREIGN PATENT DOCUMENTS

| EP | 0694528 B1 | 5/1998 |
|----|------------|--------|
| WO | WO 94/28464 | 2/1994 |
| WO | WO 98/11056 | 3/1998 |

* cited by examiner

*Primary Examiner*—Sreeni Padmanabhan
*Assistant Examiner*—Paul A. Zucker
(74) *Attorney, Agent, or Firm*—Fay, Sharpe, Fagan, Minnich & McKee, LLP

(57) ABSTRACT

The present invention provides a process for the preparation of a chelant or chelating agent complex of the formula L•B•M. L is an amino acid derivative including two optically active amino acids are linked via a $(CH2)_n$ group, wherein the $(CH2)_n$ group is attached to a nitrogen of each optically active amino acid, the optically active amino acid may be the same or different; and wherein n is an integer from 1 to 10; B is a base; and M is a metal. The process comprises the steps of (i) providing a reaction mixture comprising L and B and having a pH of less than 7.5; (ii) contacting the reaction mixture with M to provide a first complex mixture; and (iii) contacting the first complex mixture with a further amount of B to provide a second complex mixture. The second complex mixture can further be sequentially contacted with further amounts of M and further amounts of B. Alternatively, the second complex mixture can be heated.

33 Claims, No Drawings

PROCESS FOR PREPARING A COMPLEX OF A LIGAND, METAL AND BASE

This application is a continuation of U.S. Provisional Application No. 60/204,074, filed on May 12, 2000.

This invention relates to a process for the preparation of a complex comprising a ligand, a metal and a base.

As discussed in U.S. Pat. No. 5,717,123 chelants or chelating agents are compounds which form coordinate covalent bonds with a metal ion to form chelates. Chelates are coordination compounds in which a central metal atom is bonded to two or more other atoms in at least one other molecule (ligand) such that at least one heterocyclic ring is formed with the metal atom as part of each ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry.

In the bleaching stage of photographic materials, a particularly important class of bleaching agents are the aminopolycarboxylic acid bleaching agents, such as an ammonium or alkali metal salt of a ferric complex of ethylenediaminetetraacetic acid (EDTA) or of ethylenediamine disuccinic acid. The production of iron ammonium salts of EDTA is taught in U.S. Pat. No. 4,364,871 and U.S. Pat. No. 4,438,040. Ferric complex salts of propylenediaminetetraacetic acid (PDTA) having a higher bleaching power than EDTA have also been widely used as bleaching agents.

The preparation of complexes of EDDS with metals ions and bases, such as ammonia, are known in the art. For example EP-A-0641168 discloses (S,S)-ethylenediamine-N,N'-disuccinic acid iron (III) ammonium salt. This compound is represented by the formula:

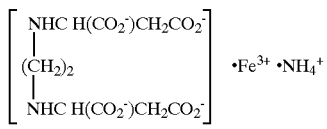

EP-A-0641168 teaches that the above compound can be synthesised by simple contact of (S,S) EDDS with ammonia and iron or an iron compound. It has been recognised in the art that such prior processes for the production of chelates comprising ligands comprising optically active amino acids, such as ethylenediamine-N,N'-disuccinic acid, may result in undesirable precipitation of insoluble oxides and/or hydroxides. This is in contrast to the production of chelates of products such as EDTA which does not result in problems of solid production.

U.S. Pat. No. 5,717,123 teaches that a concentrated stable iron chelate solution may be obtained by addition of a water soluble alkali metal salt of a polyamino disuccinic acid, for example EDDS, to an aqueous ferric salt solution.

U.S. Pat. No. 5,763,634 teaches that ferric chelate of a polyamino disuccinic acid may be prepared without insoluble oxides/hydroxides precipitating out by the simultaneous addition to a vessel of a ferric salt and an alkali metal salt of the polyamino disuccinic acid.

The present invention alleviates the problems of the prior art.

In a first aspect the present invention provides a process for the preparation of a complex of the formula

L·B·M wherein (a) L is of the formula $(R^1)(R^2)N-(CH_2)_n-N(R^3)(R^4)$, wherein each of $(R^1)(R^2)N$ and $N(R^3)(R^4)$ is an optically active amino acid, which may be the same or different; and wherein n is an integer from 1 to 10, (b) B is a base and (c) M is a metal, the process comprising the steps of (i) providing a reaction mixture comprising L and B and having a pH of less than 7.5;

(ii) contacting the reaction mixture with M to provide an first complex mixture; and (iii) contacting the first complex mixture with a further amount of B to provide a second complex mixture.

In the present specification by the term "base" it is meant a substance that can accept a proton.

It will be appreciated by one skilled in the art that L of formula L·B·M is in the form of a salt and that L used in the process of the invention may in the form of an acid of a salt thereof.

It will be appreciated that in the process of the present invention B and M can be utilised in the process in ionic, elemental and/or molecular form.

We have surprisingly found that by splitting the contact of the base B with the metal M and ligand L, such that the pH of the reaction mixture of step (i) is kept below 7.5, a process for preparing the complex is provided in which formation of solids is substantially reduced. The present process provides at least some base in the reaction mixture of step (i) and subsequently contacts further base with the mixture of metal M, base B and ligand L. The split addition ensures that the pH is retained at a level below that which results in the undesirable solid formation.

Process

Preferably the amount of B contacted with the first complex mixture in (iii), is such that the pH of the first complex mixture and/or second complex mixture has a value of less than 7.5. Preferably the amount of B provided in (i), and/or the amount of B contacted with the first complex mixture in (iii), is such that the pH of the reaction mixture, first complex mixture and/or second complex mixture has a value of from 4 to 6. In one or more steps of the invention, or in one aspect in all steps (i), (ii) and (iii) of the claimed invention, the pH of the reaction mixture has a value of less than 7.5, preferably from 4 to 6.

During addition of M, such as ferric ions in the form of ferric nitrate, and until B such as ammonia has added in step (iii) thereby raising the pH, the reaction mixture typically reaches a pH between 1 and 2. Low pH may result in decomposition of ligand L, for example of the decomposition of EDDS to lactam and ethylenediamine monosuccinate. Thus in a preferred aspect from the commencement of step (ii) until the commencement of step (iii) the reaction mixture is maintained at a temperature of no greater than 30° C.

In some aspects the present process generates as by-product oxides of M, for example oxides of iron, which are insoluble under the reaction conditions. Insoluble by-products may be removed, for example by filtration. In a preferred aspect to minimise the amount of solids produced and/or to ease their filtration, the process provides a stoichiometric excess of L, such as for example ethylenediamine disuccinic acid, over M, for example ferric ion. In a preferred aspect the ratio of M to L is 0.95 to 0.85.

In one aspect the process further comprises the step of heating the second complex mixture. In this preferred aspect the second complex mixture may be heated to a temperature of 60–100° C., preferably 70–90° C., more preferably approximately 80° C.

When the second complex mixture is heated, in one aspect it may be heated for a period of 30 to 90 minutes, typically for 45 to 75 minutes, or typically approximately 60 minutes.

After the constituents of the complex forming mixture have been contacted and the mixture has been optionally heated as discussed above, the process of the present invention preferably comprises the further step of adjusting the pH of second complex mixture to a value of from 6 to 7.5 or 6 to 7.

The reaction medium (reaction mixture/first complex mixture/second complex mixture) of the present invention is normally wholly aqueous but the presence of other solvents such as ethanol is not excluded.

The process of the present invention may comprise further steps of sequentially contacting the second complex mixture with a further amount of M and a further amount of B. In this way further control of the pH and solid formation may be exercised.

Ligand L

L is of the formula $(R^1)(R^2)N$—$(CH_2)_n$—$N(R^3)(R^4)$ wherein each of $(R^1)(R^2)N$ and $N(R^3)(R^4)$ is an optically active amino acid, which may be the same or different. Preferably n is 2, 3 or 4.

The amino acids will normally be one of the 25 or so naturally occurring optically active amino acids listed in standard textbooks viz. alanine, valine, leucine, norleucine, phenylalanine, tyrosine, serine, cystine, threonine, methionine, di-iodotyrosine, thyroxine, dibromotyrosine, tryptophan, proline and hydroxyproline (which are all "neutral"), aspartic acid, glutamic acid and β-hydroxyglutamic acid (which are all "acidic") and ornithine, arginine, lysine and histidine (which are all "basic" and less preferred for the reasons stated below). All these acids have an α-amino group but other amino acids e.g. phenylglycine or amino acids having a β-amino group such as β-alanine can be used. The preferred amino acids are those with two carboxyl groups and one amino group (preferably the "acidic" amino acids listed above). Aspartic and glutamic acid are the most preferred of the three. The "basic" amino acids have more potential for unwanted side reactions and are currently less preferred than the "neutral" amino acids. In the case of synthetic amino acids substituted hydrocarbyl groups may be present. Specific optical isomers, particularly the L-form, are desirable because they increase biodegradability and in some cases, may also improve the chelating effect.

Preferably L is optically active.

Preferably L is in the S isomeric form. More preferably L is in the S,S isomeric form.

Ligand L may be selected from ethylenediamine N,N'-disuccinic acid (EDDS), diethylenetriamine-N,N''-disuccinic acid, triethylenetetraamine-N,N'''-disuccinic acid, 1,6-hexamethylenediamine-N,N'-disuccinic acid, tetraethylenepentamine-N,N'''-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, ciscyclohexanediamine N,N'-disuccinic acid, trans-cyclohexanediamine N,N'-disuccinic acid, and ethylenebis(oxyethylene-nitrilo)-N,N'-disuccinic acid.

Preferably L is ethylenediamine N,N'-disuccinic acid (EDDS).

Preferably L is (S,S)-ethylenediamine N,N'-disuccinic acid or a salt thereof.

In one aspect the ligand L may be prepared in accordance with the teaching of WO 95/12570. The ligand L may be an amino acid derivatives in free acid or salt form, wherein L is prepared by a process in which the nitrogen atoms of two or more amino acid molecules are linked by a hydrocarbyl or substituted hydrocarbyl group, which comprises reacting, in an aqueous medium at a pH in the range 7–14 and preferably in aqueous alkali, a compound of the formula X-A-Y where X and Y are halo atoms which may be the same or different and A is a hydrocarbyl or substituted hydrocarbyl group in which X and Y are attached to aliphatic or cycloaliphatic carbon atoms, with an amino acid (or salt thereof), wherein the reaction is carried out in the presence of dissolved cations of an alkaline earth metal or of a transition metal.

Ligands for use in the present invention may be prepared, for instance, by the process disclosed U.S. Pat. No. 3,158,635. U.S. Pat. No. 3,158,635 discloses reacting maleic anhydride (or ester or salt) with a polyamine corresponding to the desired polyamino disuccinic acid under alkaline conditions. The reaction yields a number of optical isomers, for example, the reaction of ethylenediamine with maleic anhydride yields a mixture of three optical isomers [R,R], [S,S] and [S,R] ethylenediamine disuccinic acid (EDDS) because there are two asymmetric carbon atoms in ethylenediamine disuccinic acid. These mixtures are used as mixtures or alternatively separated by means within the state of the art to obtain the desired isomer(s). Alternatively, [S,S] isomers are prepared by reaction of such acids as L-aspartic acid with such compounds as 1,2-dibromoethane as described by Neal and Rose, "Stereospecific Ligands and Their Complexes of Ethylenediaminedisuccinic Acid", Inorganic Chemistry, v. 7. (1968), pp. 2405–2412.

Base B

Preferably the base of the process of the present invention B is selected from ammonia, ammonium compounds (including ammonium hydroxide), organic amines, sodium hydroxide, potassium hydroxide and mixtures thereof.

Metal M

Preferably the metal of the process of the present invention M is iron.

In the process the metal M may be provided in elemental, ionic or molecular form. In any of these forms the metal may be provided in the oxidation state which it is to have in the complex. Alternatively, it may be provided in a different oxidation state to that which it will have in the complex. In this latter aspect the process may comprise a step of modifying the oxidation state of the metal. The modification may be an oxidation.

Preferably the metal is a transition metal. More preferably is iron.

In a preferred aspect the metal M of the formula L·B·M is a transition metal ion. In a more preferred aspect the metal M of the formula L·B·M is an iron ion, in particular $Fe^{2+}$ and/or $Fe^{3+}$. In a highly preferred aspect the metal M of the formula L·B·M is $Fe^{3+}$.

Further Preferred Aspects

In further preferred aspects L, B and M are as defined below.

L is an optically active compound is of the formula

wherein each of $(R^1)(R^2)N$ and $N(R^3)(R^4)$ is an optically active amino acid, which may be the same or different; and wherein n is an integer from 1 to 10 preferably n is 2, 3 or 4;

B is ammonia/ammonium; and

M is a transition metal ion
L is the S,S isomeric form of a compound is of the formula

wherein each of $(R^1)(R^2)N$ and $N(R^3)(R^4)$ is an optically active amino acid, which may be the same or different; and wherein n is an integer from 1 to 10, preferably n is 2, 3 or 4;
B is ammonia/ammonium; and
M is a transition metal ion
L is ethylenediamine N,N'-disuccinic acid (EDDS);
B is ammonia/ammonium; and
M is a transition metal ion
L is (S,S) ethylenediamine N,N'-disuccinic acid (EDDS);
B is ammonia/ammonium; and
M is a transition metal ion
L is an optically active compound of the formula

wherein each of $(R^1)(R^2)N$ and $N(R^3)(R^4)$ is an optically active amino acid, which may be the same or different; and wherein n is an integer from 1 to 10, preferably n is 2, 3 or 4;
B is ammonia/ammonium; and
M is iron
L is the S,S isomeric form of a compound is of the formula

wherein each of $(R^1)(R^2)N$ and $N(R^3)(R^4)$ is an optically active amino acid, which may be the same or different; and wherein n is an integer from 1 to 10, preferably n is 2, 3 or 4;
B is ammonia/ammonium; and
M is iron
L is ethylenediamine N,N'-disuccinic acid (EDDS);
B is ammonia/ammonium; and
M is iron
L is (S,S) ethylenediamine N,N'-disuccinic acid (EDDS);
B is ammonia/ammonium; and
M is iron
L is an optically active compound of the formula

wherein each of $(R^1)(R^2)N$ and $N(R^3)(R^4)$ is an optically active amino acid, which may be the same or different; and wherein n is an integer from 1 to 10, preferably n is 2, 3 or 4;
B is ammonia/ammonium; and
M is $Fe^{2+}$ or $Fe^{3+}$, preferably $Fe^{3+}$ L is the S,S isomeric form of a compound is of the formula

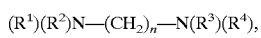

wherein each of $(R^1)(R^2)N$ and $N(R^3)(R^4)$ is an optically active amino acid, which may be the same or different; and wherein n is an integer from 1 to 10, preferably n is 2, 3 or 4;
B is ammonia/ammonium; and
M is $Fe^{2+}$ or $Fe^{3+}$, preferably $Fe^{3+}$
L is ethylenediamine N,N'-disuccinic acid (EDDS);
B is ammonia/ammonium; and
M is $Fe^{2+}$ or $Fe^{3+}$, preferably $Fe^{3+}$
L is (S,S) ethylenediamine N,N'-disuccinic acid (EDDS);
B is ammonia/ammonium; and
M is $Fe^{2+}$ or $Fe^{3+}$, preferably $Fe^{3+}$ The process of this invention is illustrated by the following Examples. In each of the examples "EDDS" means (S,S)-ethylenediaminedisuccinic acid, i.e. a compound of formula:

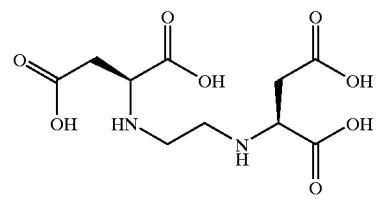

EXAMPLES

Examples 1 to 4

Examples 1 to 4 are a series of experiments showing
in comparison examples 1 and 2 the high level of solids produced by the non-sequential addition of components and/or addition to increase the pH to above 7.5 and
in examples 3 and 4 the low amount of solids produced by sequential addition in accordance with the present invention.

Procedure

Stage 1—into a glass reaction vessel is charged ethylene diamine disuccinic acid and water followed by aqueous ammonia solution with stirring.
Stage 2—to the so formed mixture is added a solution of ferric nitrate nonahydrate in water over 1–2 hours
Stage 3—further aqueous ammonia is added
Stage 4—the reaction mixture is heated to 80° C. for 1 hour then following cooling pH is adjusted to 6.5 to 7.5. The solution is filtered to give a clear product solution and insoluble material.

| | EXAMPLE | 1 (COMPARISON) | 2 (COMPARISON) | 3 | 4 |
|---|---|---|---|---|---|
| STAGE 1 | Wt wet cake EDDS (g) | 78 | 78 | 78 | 78 |
| | EDDS content % | 86.16 | 86.16 | 86.16 | 86.16 |
| | Wt EDDS in cake (g) | 67.2 | 67.2 | 67.2 | 67.2 |
| | Moles EDDS | 0.23 | 0.23 | 0.23 | 0.23 |
| | Wt water charged (g) | 124 | 110 | 154 | 137 |
| | Ammonia solution charged (g) | 45.4 | 60.5 | 15 | 30 |
| | Concentration of ammonia solution % w/w | 25.85 | 25.85 | 25.85 | 25.85 |
| | Moles ammonia charged | 0.69 | 0.92 | 0.23 | 0.46 |

-continued

| | EXAMPLE | 1 (COMPARISON) | 2 (COMPARISON) | 3 | 4 |
|---|---|---|---|---|---|
| | pH resulting | 9.56 | 10.15 | 5.56 | 6.51 |
| STAGE 2 | Wt Fe(NO$_3$)3.9H$_2$O (g) | 94.5 | 94.5 | 94.5 | 94.5 |
| | Wt water (g) | 50 | 50 | 50 | 50 |
| | Moles Fe charged | 0.23 | 0.23 | 0.23 | 0.23 |
| | pH resulting | 2.3 | 4.95 | 0.82 | 1.9 |
| STAGE 3 | Ammonia solution charged (g) | 15 | 0 | 45 | 30 |
| | Concentration of ammonia solution % w/w | 25.85 | | 25.85 | 25.85 |
| | Moles ammonia solution charged | 0.23 | | 0.69 | 0.23 |
| | pH resulting | 4.90 | | 6.60 | 4.4 |
| STAGE 4 | Final pH | 7.01 | 7.01 | 6.78 | 6.8 |
| | Wt final solution (g) | 368.5 | 377.5 | 422.0 | 4.9 |
| | Wt solids (g) | 1.5 | 1.5 | 0.5 | 0.5 |

Example 5

These examples were following the procedure below, which exemplifies a stoichiometry of Fe to EDDS of 0.95.

Into a 1 liter reaction flask equipped with pH probe, overhead stirrer and temperature probe was charged with 360 g EDDS wet cake (at 68% EDDS content equivalent to 244.8 g, 0.838 moles), 360 g water. Agitator started and ammonia solution (30% w/w) added to reach a pH of 6.5. A solution of ferric nitrate (9.2% w/w ferric ion, 487 g, 0.800 moles) was added via peristaltic pump over two hours.

Further ammonia solution was then added to reach pH 6.50 again. Reaction mixture was heated to 80° C. and held for 1 hour before cooling to less than 35° C. Further ammonia was added to bring pH to 7. Reaction mixture was filtered through 11 cm No54 Whatman filter paper.

| Example | A | B | C | D | E |
|---|---|---|---|---|---|
| Mole ratio Fe:EDDS | 1.00 | 0.94 | 0.90 | 0.85 | 0.80 |
| Wt product (g) | 1410.4 | 1418.3 | 1356.1 | 1321.8 | 1283.2 |
| Wt solids (g) | 18.80 | 5.70 | 2.28 | 0.48 | <0.1 |
| Filtration time (mins) | 2.0 | 1.4 | 0.8 | 0.5 | >10 |

We demonstrated the influence of iron to EDDS stoichiometry on filterability.

Example 6

To a 220 glass lined reactor is charged 65.115 kg wet cake EDDS (59.326 kg at 33.2 % LOD and 5.789 kg at 34.10% LOD) followed by 51.4 kg water. The agitator was started and aqueous ammonia was charged to pH 6.30 16.24 kg (31% solution). Temperature rose from 22.8 to 28.9° C. Ferric nitrate solution (9.19% w/w Fe) was charged over 3 hours, (81.1 kg), temperature was below 29° C. Further ammonia was charged to the reactor to reach a pH of 7.2 (15.02 kg), temperature rose to 37.9° C. Reactor was discharged through a 10 micron stainless steel filter to yield 216.3 kg clear brown solution. The material had ferric content of 3.23% w/w. Both lactam and ethylenediamine monosuccinate (EDMS) were below 0.1 g/l.

Example 7 (Comparison)

To a stirred slurry of 81.7 g EDTA in 172 g water was added 74.0 g ammonia solution (26.8%) to give a solution with pH of 10.1. A solution of ferric nitrate 166.7 g (9.5% w/w iron content) was added over 10 minutes producing a dark solution. The material was stirred for 25 minutes followed by heating at 80° C. for 1 hour. The mixture was cooled and pH adjusted to pH 7. The material was filtered through No 41 Whatman paper to give a clear solution 482 g and a small amount of solids, <0.05 g. The solution had ferric content of 3.1% w/w.

This example demonstrates that in contrast to the specific compounds of the present invention, complexes of EDTA may be synthesised by simple addition of the complex components without the problem of high solid formation.

Example 8 (Comparison)

To a stirred slurry of 81.8 g EDTA in 174 g water was added 36.0 g of ammonia solution (26.8% w/w). To the so produced solution (pH 5.96) was added 168.1 g of ferric nitrate solution (9.5% w/w iron content). The mixture was stirred for 10 minutes then a further 36.2 g ammonia solution was added producing a dark solution. The solution was heated at 80° C. for 1 hour before being filtered through 7 cm dia No. 41 Whatman filter paper. Only a small amount of solids were produced, <0.05 g. The solution had ferric content 3.2% w/w and weighed 474 g.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

What is claimed is:

1. A process for the preparation of a complex of the formula

L·B·M wherein
(a) L is an amino acid derivative including two optically active amino acids linked by a (CH$_2$)$_n$ group, wherein the (CH$_2$)$_n$ group is attached to a nitrogen of each optically active amino acid, said optically active amino acid may be the same or different;

and wherein n is an integer from 1 to 10, (b) B is a base and (c) M is a metal, the process comprising the steps of (i) providing a reaction mixture comprising L and B and having a pH of less than 7.5;

(ii) contacting the reaction mixture with M to provide a first complex mixture;

(iii) contacting the first complex mixture with a further amount of B to provide a second complex mixture; and (iv) sequentially contacting the second complex mixture with further amounts of M and further amounts of B.

2. The process according to claim 1 wherein the amount of B contacted with the first complex mixture in (iii), is such that the pH of at least one of the first complex mixture and second complex mixture has a value of less than 7.5.

3. The process according to claim 2 wherein the amount of B provided in (i), and/or the amount of B contacted with the first complex mixture in (iii), is such the pH of the reaction mixture, first complex mixture and/or second complex mixture is from 4 to 6.

4. The process according to claim 1, wherein after complete addition of M, B and L, the process further comprises the step of: adjusting the pH of second complex mixture to a value of from 6 to 7.

5. The process according to claim 1 wherein the amino acid is a naturally-occurring amino acid.

6. The process according to claim 1 wherein the amino acid is aspartic acid or glutamic acid.

7. The process according to claim 1 wherein L is in the S isometric form.

8. The process according to claim 1 wherein L is in the S,S isometric form.

9. The process according to claim 1 wherein L is ethylenediaminedisuccinic acid or a salt thereof.

10. The process according to claim 1 wherein L is (S,S)-ethylenediaminedisuccinic acid or a salt thereof.

11. The process according to claim 1 wherein B is selected from the group consisting of ammonia, ammonium compounds, organic amines, sodium hydroxide, potassium hydroxide and mixtures thereof.

12. The process according to claim 1 wherein B is ammonia.

13. The process according to claim 1 wherein M is iron.

14. The process according to claim 1 further comprising the step of subjecting at least one of the reaction mixture, first complex mixture and second complex mixture to oxidizing conditions to increase the oxidation state M.

15. A process for the preparation of a complex of the formula

L·B·M wherein (a) L is an amino acid derivative including two optically active amino acids linked by a $(CH_2)_n$ group, wherein the $(CH_2)_n$ group is attached to a nitrogen of each optically active amino acid, said optically active amino acid may be the same different;

and wherein n is an integer from 1 to 10, (b) B is a base and (c) M is a metal, the process comprising the steps of (i) providing a reaction mixture comprising L and B and having a pH of less than 7.5;

(ii) contacting the reaction mixture with M to provide a first complex mixture;

(iii) contacting the first complex mixture with a further amount of B to provide a second complex mixture; and (iv) heating the second complex mixture.

16. The process according to claim 15 wherein the amount of B contacted with the first complex mixture in (iii), is such that the pH of at least one of the first complex mixture and second complex mixture has a value of less than 7.5.

17. The process according to claim 15 wherein the amount of B provided in (i), and/or the amount of B contacted with the first complex mixture in (iii), is such the pH of the reaction mixture, first complex mixture and/or second complex mixture is from 4 to 6.

18. The process according to claim 15 wherein the second complex mixture is heated to a temperature of 60–100° C.

19. The process according to claim 15 wherein the second complex mixture is heated for a period of 30 to 90 minutes.

20. The process according to claim 15 wherein after complete addition of M, B and L, the process further comprises the step of:

adjusting the pH second complex mixture to a value of from 6 to 7.

21. The process according to claim 15 wherein the amino acid is a naturally-occurring amino acid.

22. The process according to claim 15 wherein the amino acid is aspartic acid or glutamic acid.

23. The process according to claim 15 wherein L is in the S isometric form.

24. The process according to claim 15 wherein L is in the S,S isometric form.

25. The process according to claim 15 wherein L is ethylenediaminedisuccinic acid or a salt thereof.

26. The process according to claim 15 wherein L is (S,S)-ethylenediaminedisuccinic acid or a salt thereof.

27. The process according to claim 15 wherein B is selected from the group consisting of ammonia, ammonium compounds, organic amines, sodium hydroxide, potassium hydroxide and mixtures thereof.

28. The process according to claim 26 wherein B is ammonia.

29. The process according to claim 28 wherein M is iron.

30. The process according to claim 15 further comprising the step of subjecting at least one of the reaction mixture, first complex mixture and second complex mixture to oxidizing conditions to increase the oxidation state M.

31. A process according to claim 18 wherein the second complex mixture is heated to a temperature of 70–90° C.

32. A process according to claim 11 wherein the ammonium compound is ammonium hydroxide.

33. A process according to claim 27 wherein the ammonium compound is ammonium hydroxide.

* * * * *